(12) United States Patent
Kang et al.

(10) Patent No.: US 12,097,385 B2
(45) Date of Patent: Sep. 24, 2024

(54) LUNG PHANTOM UNIT FOR RADIOTHERAPY

(71) Applicant: THE CATHOLIC UNIVERSITY OF KOREA INDUSTRY-ACADEMIC COOPERATION FOUNDATION, Seoul (KR)

(72) Inventors: Young Nam Kang, Seoul (KR); Tae Geon Oh, Gyeonggi-do (KR); Yun Ji Seol, Gyeonggi-do (KR); Na Young An, Seoul (KR); Jae Hyeon Lee, Seoul (KR); Chul Seung Kay, Gyeonggi-do (KR); Jin Sol Shin, Incheon (KR); Jin Ho Hwang, Incheon (KR); Hun Joo Shin, Incheon (KR); Myung Ho Kim, Seoul (KR); Hong Seok Jang, Seoul (KR)

(73) Assignee: THE CATHOLIC UNIVERSITY OF KOREA INDUSTRY-ACADEMIC COOPERATION FOUNDATION, Seoul (KR)

( * ) Notice: Subject to any disclaimer, the term of this patent is extended or adjusted under 35 U.S.C. 154(b) by 257 days.

(21) Appl. No.: 17/781,842

(22) PCT Filed: Oct. 8, 2020

(86) PCT No.: PCT/KR2020/013702
§ 371 (c)(1),
(2) Date: Jun. 2, 2022

(87) PCT Pub. No.: WO2021/112387
PCT Pub. Date: Jun. 10, 2021

(65) Prior Publication Data
US 2023/0008391 A1  Jan. 12, 2023

(30) Foreign Application Priority Data
Dec. 3, 2019 (KR) .......................... 10-2019-0159217

(51) Int. Cl.
*A61N 5/10* (2006.01)

(52) U.S. Cl.
CPC ........ *A61N 5/10* (2013.01); *A61N 2005/1076* (2013.01)

(58) Field of Classification Search
CPC ........................................................ A61N 5/10
See application file for complete search history.

(56) References Cited

U.S. PATENT DOCUMENTS

| 2008/0298540 | A1* | 12/2008 | Serban | A61N 5/1048 378/18 |
| 2017/0042502 | A1* | 2/2017 | Koo | A61B 6/032 |
| 2017/0169734 | A1* | 6/2017 | Wen | G09B 23/32 |

FOREIGN PATENT DOCUMENTS

| KR | 10-1018880 B1 | 3/2011 |
| KR | 10-1597141 B1 | 2/2016 |

(Continued)

OTHER PUBLICATIONS

International Search Report for PCT/KR2020/013702 mailed on Feb. 1, 2021.

*Primary Examiner* — Hugh Maupin
(74) *Attorney, Agent, or Firm* — The PL Law Group, PLLC (57) ABSTRACT

A lung phantom unit for radiotherapy according to an embodiment of the present disclosure may arrange, at a location not affected by a magnetic field, a phantom driving cylinder and a driving device which may move a lung mimic and a tumor mimic in a lung simulation block. The lung phantom unit may be used for general purpose even as a phantom for MRI-based and CT image-based radiotherapy. Since lung and tumor motions are implemented by air injection, it may be possible to precisely measure the motion and volume change of a lung according to subtle changes in (Continued)

air pressure so that customized radiotherapy suitable for a patient having various breathing patterns is possible.

7 Claims, 7 Drawing Sheets

(56) References Cited

FOREIGN PATENT DOCUMENTS

| | | |
|---|---|---|
| KR | 10-1697430 B1 | 1/2017 |
| KR | 10-1721668 B1 | 4/2017 |
| KR | 10-1741946 B1 | 5/2017 |
| KR | 10-2017-0118394 A | 10/2017 |

* cited by examiner

LUNG PHANTOM UNIT FOR RADIOTHERAPY

CROSS REFERENCE TO RELATED APPLICATIONS AND CLAIM OF PRIORITY

This application claims benefit under 35 U.S.C. 119, 120, 121, or 365(c), and is a National Stage entry from International Application No. PCT/KR2020/013702, filed Oct. 8, 2020, which claims priority to the benefit of Korean Patent Application No. 10-2019-0159217 filed in the Korean Intellectual Property Office on Dec. 3, 2019, the entire contents of which are incorporated herein by reference.

BACKGROUND

1. Technical Field

The present invention relates to a lung phantom unit for radiotherapy, and more particularly, to a lung phantom unit for radiotherapy having an improved structure, so as to operate smoothly without being affected by a magnetic field or an electric field generated from electronic equipment such as MRI or CT used in radiotherapy.

2. Background Art

Although 4D-CT images are used for general respiratory gated radiotherapy, there is a disadvantage in that it is difficult to distinguish the anatomical structure of soft tissues. On the other hand, MRI images do not have radiation exposure and have high contrast in soft tissues compared to CT images, and thus MRI images have the advantage of being able to accurately describe soft tissues and tumors.

The development and commercialization of MRI-LINAC and MR-Simulator, which are radiotherapy devices based on MRI images having the advantage, are in progress.

Accordingly, there is a need for a QA phantom for quality maintenance and precision evaluation of MRI-based radiotherapy devices.

However, it is impossible to use the existing CT-based phantom because the existing CT-based phantom for radiotherapy has motors and components made of a metal material, and MRI uses a strong magnetic field (equal to or greater than 0.35 T).

Therefore, the development of a phantom for quality maintenance and precision evaluation used in MRI-based radiotherapy is required.

SUMMARY

The present invention has been devised to solve the above problems, and provides a lung phantom unit for radiotherapy so as to operate smoothly without being affected by a magnetic field or an electric field generated from electronic equipment such as MRI or CT used in radiotherapy.

According to an aspect of the present disclosure, a lung phantom unit for radiotherapy includes a lung simulation block including a phantom human mimic filled with a liquid inside, a lung mimic accommodated in the phantom human mimic and contracted and expanded according to an inflow of external air, and a tumor mimic disposed inside the lung mimic; a phantom driving cylinder fluid-movably connected to the lung mimic at a position spaced apart from the lung simulation block; a driving device for compressing and expanding air accommodated in the phantom driving cylinder; and a connection tube having one side communicatively connected to the phantom driving cylinder and the other side communicatively connected to the lung simulation block and formed to have a long length along a central axis direction of the phantom human mimic, so that an operation of the driving device is not affected by a magnetic field or an electric field formed by a capturing unit for securing an image of the lung simulation block.

The driving device may include a motor; a pressing disk movably installed in a chamber and moved by receiving power of the motor so as to compress and expand the air accommodated in the phantom driving cylinder; and a pressing rod having one side connected to the motor and the other end connected to the pressing disk so as to be moved together with the pressing disk, to dynamically connect the motor and the pressing disk.

The driving device may include a nut member provided on the pressing rod; and a transfer screw formed long along an axis in one direction, connected to a drive shaft so as to be rotated together with the drive shaft of the motor, and screw-coupled with the nut member.

The lung phantom unit for radiotherapy may further include a sensing tube communicatively connected to the lung mimic and the phantom driving cylinder; and a lifting member comprising a rod portion installed on the sensing tube to be liftable and formed long along a lifting direction, and a mounting portion formed as a plate structure on an upper side of the rod portion and on which an object that enables image capture with respect to a lifting operation is placed.

The lung simulation block may be made of a non-metal material.

The connection tube may be in the form of a flexible corrugated tube so that length expansion and contraction is possible.

The lung phantom unit for radiotherapy may further include a first shelf on which the lung simulation block is installed and a second shelf on which the driving device is installed, wherein the first shelf and the second shelf are installed to be movable relative to each other so as to enable length adjustment.

The lung phantom unit for radiotherapy may further include a first shelf on which the lung simulation block is installed and a second shelf on which the driving device is installed, wherein the first shelf and the second shelf are installed to be rotatable relative to each other so as to enable angle adjustment.

The lung phantom unit for radiotherapy according to the present invention having the configuration as described above has the effects of enabling a phantom driving cylinder and a driving device, which may move a lung mimic and a tumor mimic in a lung simulation block, to be used for general purpose even as a phantom for MRI-based and CT image-based radiotherapy by arranging the phantom driving cylinder and the driving device at a location not affected by a magnetic field, from the lung simulation block, which is a part from which the magnetic field is generated when an MRI is performed or a part from which an electric field is generated when a CT is performed, and, since lung and tumor motions are implemented by air injection, enabling the motion and volume change of a lung according to subtle changes in air pressure to be precisely measured so that customized radiotherapy suitable for a patient having various breathing patterns is possible.

DETAILED DESCRIPTION

In the following description, in order to clarify the understanding of the present invention, descriptions of well-known techniques for the features of the present invention will be omitted. The following embodiments are the detailed descriptions to help the understanding of the present invention, and will not naturally limit the scope of the present invention. Accordingly, equivalent inventions performing the same functions as the present invention will also fall within the scope of the present invention.

In addition, in the following description, the same reference numerals mean the same configurations, and unnecessary redundant descriptions and descriptions of well-known technologies will be omitted. In addition, the description of each embodiment of the present invention that overlaps with the description of the technology that is the background of the invention will also be omitted.

Hereinafter, a lung phantom unit for radiotherapy according to an embodiment of the present invention will be described in detail with reference to the accompanying drawings.

Figure 1:
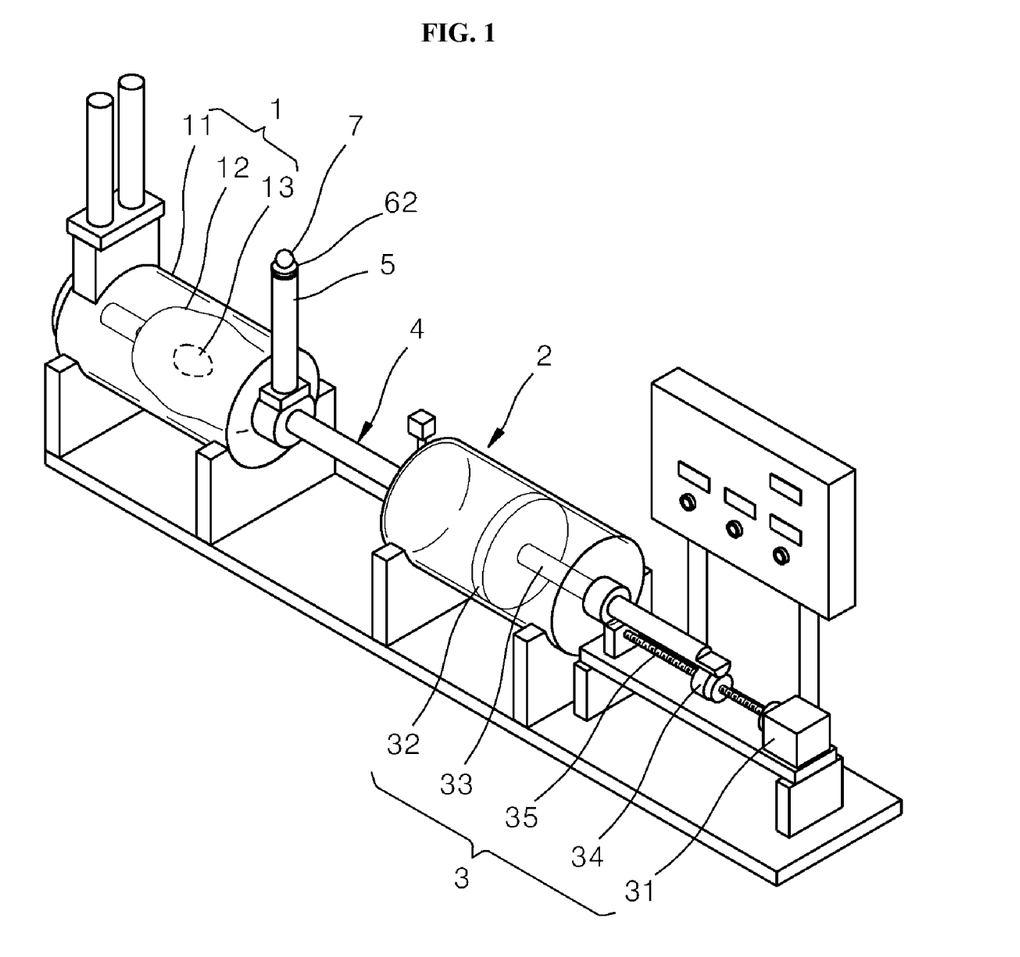
FIG. 1 is a perspective view of a lung phantom unit for radiotherapy according to an embodiment of the present invention.
Figure 2:
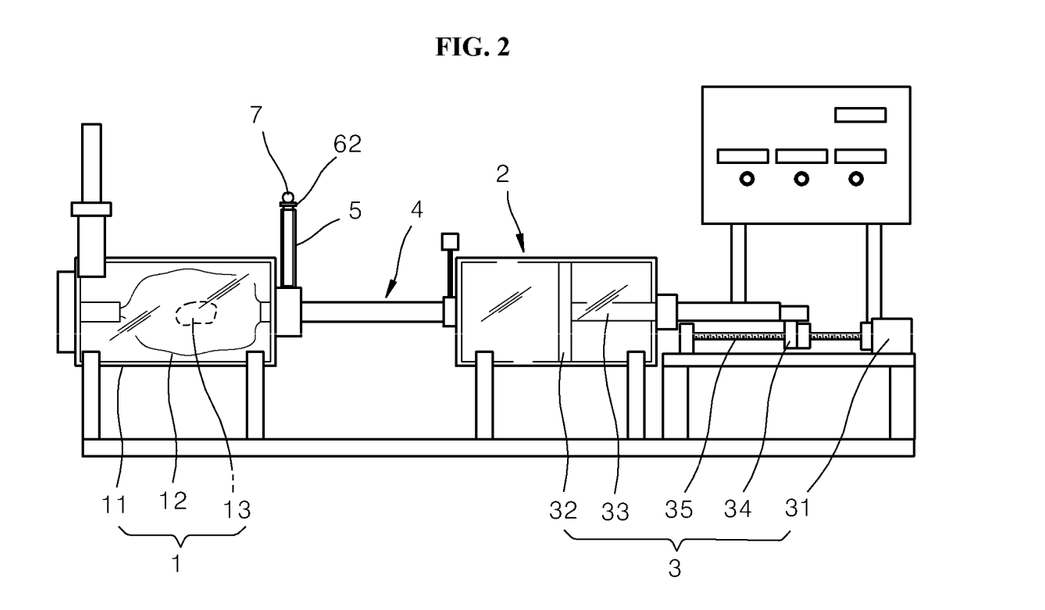
FIG. 2 is a front view of an embodiment of the present invention.
Figure 3:
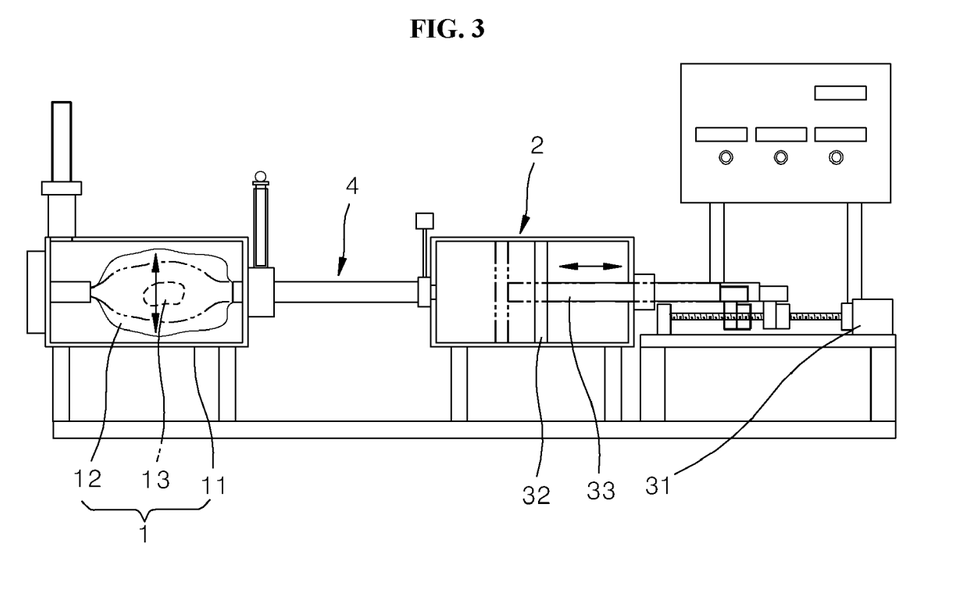
FIG. 3 is a view for explaining an operating state of an embodiment of the present invention.
Figure 4:
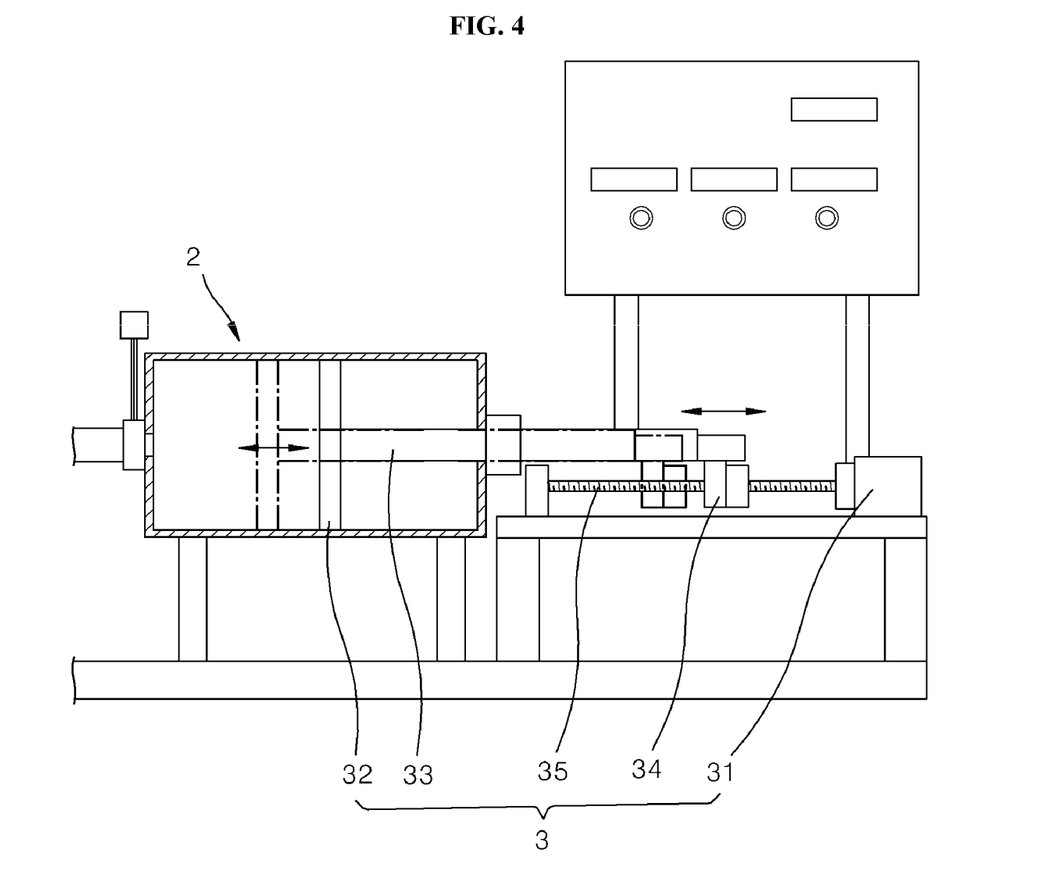
FIG. 4 is an enlarged view showing a driving device and a phantom driving cylinder employed in an embodiment of the present invention.
Figure 5:
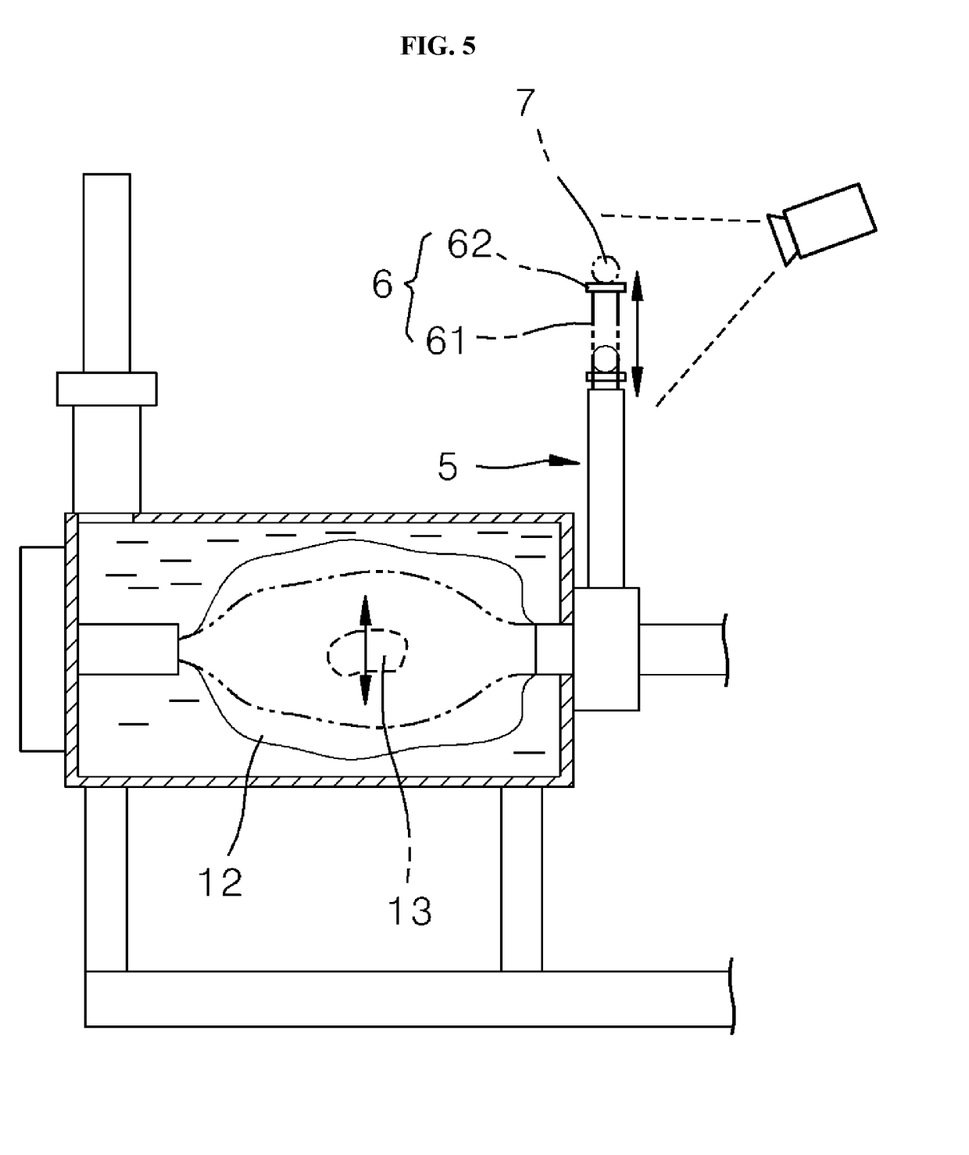
FIG. 5 is a view for explaining an operating state of a sensing tube and a lifting member employed in an embodiment of the present invention.

FIG. 1 is a perspective view of a lung phantom unit for radiotherapy according to an embodiment of the present invention, FIG. 2 is a front view of an embodiment of the present invention, FIG. 3 is a view for explaining an operating state of an embodiment of the present invention, FIG. 4 is an enlarged view showing a driving device and a phantom driving cylinder employed in an embodiment of the present invention, and FIG. 5 is a view for explaining an operating state of a sensing tube and a lifting member employed in an embodiment of the present invention.

As shown in FIGS. 1 and 2, the lung phantom unit for radiotherapy according to an embodiment of the present invention includes a lung simulation block 1, a phantom driving cylinder 2, a driving device 3, and a connection tube 4.

The lung simulation block 1 includes a phantom human mimic 11 filled with a liquid inside, a lung mimic 12 accommodated in the phantom human mimic 11, and a tumor mimic 13 disposed inside the lung mimic 12.

The lung mimic 12, which is contracted and expanded according to the inflow of external air, may have an exterior made of a waterproof latex material, and an inside filled with, for example, a sponge, to maintain a lung shape.

The tumor mimic 13 moves together with the lung mimic 12 and changes its shape to enable a changing shape of the tumor to be identified through a captured image. Such a tumor mimic 13 is manufactured in a slime or gel state to mimic a tumor having actual variability or is formed by filling a pouch of the latex material with water, so that its shape is deformed according to the contraction or expansion of the lung mimic 12.

A radiation contrast agent may be additionally injected into the tumor mimic 13. The contrast agent is drug that makes tissues or blood vessels more visible during radiographic inspection. When the contrast agent is injected into the tumor mimic 13, a movement of the tumor mimic 13 according to the contraction or expansion of the lung mimic 12 may be observed more precisely.

The phantom driving cylinder 2 employed in the present embodiment is movably connected to the lung mimic 12 at a position spaced apart from the lung simulation block 1, and includes space through which air may enter and exit.

The driving device 3 includes, for example, a power source such as a motor 31 to compress and expand the air accommodated in the phantom driving cylinder 2.

The connection tube 4 is formed to have a long length along the central axis of the phantom human mimic 11, and has one side communicatively connected to the phantom driving cylinder 2, and the other side is communicatively connected to the lung simulation block 1.

The connection tube 4 allows the phantom driving cylinder 2 to be disposed at a position relatively far from the lung simulating block 1 in which imaging by MRI or CT is performed together with the driving device 3, so that an operation of the driving device 3 is not affected by a magnetic field or an electric field formed by a capturing unit for securing an image of the lung simulation block 1.

The lung phantom unit for radiotherapy according to an embodiment of the present invention having such a configuration may make it possible to expect the advantage of enabling a phantom driving cylinder and a driving device, which may move the lung mimic 12 and the tumor mimic 13 in the lung simulation block 1, to be used for general purpose even as a phantom for MRI-based and CT image-based radiotherapy by arranging the phantom driving cylinder 2 and the driving device 3 at a location not affected by a magnetic field, from the lung simulation block 1, which is a part from which the magnetic field is generated when an MRI is performed or a part from which an electric field is generated when a CT is performed.

In addition, since lung and tumor motions have been implemented by air injection, the present embodiment has the advantage of enabling the motion and volume change of a lung according to subtle changes in air pressure to be precisely measured so that customized radiotherapy suitable for a patient having various breathing patterns is possible.

The lung simulation block 1 employed in the present embodiment is made of a non-metal material, so that, for example, MRI-based radiotherapy is smoothly possible without being affected by the magnetic field.

The driving device 3 may be implemented by various configurations, but in the present embodiment, has been implemented by the configuration including the motor 31, a pressing disk 32, and a pressing rod 33.

As well shown in FIGS. 3 and 4, the motor 31 corresponds to a power source, and the pressure disk 32 is movably installed in the phantom driving cylinder 2 and moved by receiving the power of the motor 31, and serves to compress and expand the air accommodated in the phantom driving cylinder 2.

The pressing rod 33 has one side connected to the motor 31 and the other side connected to the pressing disk 32 so as to be moved together with the pressing disk 32, and serves to dynamically connect the motor 31 and the pressing disk 32.

In the present embodiment having such a configuration, the pressing rod 33 is moved along the central axis direction of the phantom driving cylinder 2 by the driving of the motor 31, and the pressure disk 32 moves within the phantom driving cylinder 2 together with the pressing rod 33, so that air accommodated in a chamber is compressed or expanded.

A change in air pressure in the phantom driving cylinder 2 affects the internal pressure of the lung mimic 12 through the connection tube 4, which causes changes in movements of the lung mimic 12 and the tumor mimic 13.

As described above, the present embodiment may implement the movement of the lung during actual respiration by the change the air pressure, and change the air pressure to suit different actual breathing conditions for each patient, thereby expending the advantage of mimicking the movement corresponding to the movement of the actual lung and tumor.

The driving device 3 employed in the present embodiment, as well shown in FIG. 4, preferably further includes a nut member 34 provided on the pressing rod 33 and a transfer screw 35 screw-coupled with the nut member 34. The transfer screw 35 is formed to be elongated along the axis in one direction, is connected to a drive shaft so as to be rotated together with the drive shaft of the motor 31, and is screw-coupled with the nut member 34.

The present embodiment having such a configuration, in which the power of the motor 31 may be transferred to the pressing rod 33 through the transfer screw 35 and the nut member 34, has the advantage of allowing the motor 31 which is a power source to be disposed at a position relatively far from the lung simulation block 1.

On the other hand, as shown in FIG. 5, the present embodiment includes the sensing tube 5 as sensing means for sensing a vertical movement pattern of the lung simulation block 12 and the lifting member 6.

That is, apart from securing the movements of the lung mimic 12 and the tumor mimic 13 as MRI images, there is a need to sense a change pattern of the vertical movement of the actual lung mimic 12 to detect irregularities in breathing, etc.

The sensing tube 5 employed in the present embodiment for sensing the breathing pattern is communicatively connected to the lung base 12 and the phantom driving cylinder 2, and the lifting member 6 includes a rod portion 61 and a mounting portion 62.

The rod portion 61 is a portion that is installed on the sensing tube 5 to be liftable and is formed long along a lifting direction, and the mounting portion 62 is a portion formed as a plate structure on an upper side of the rod portion 61 and on which an object 7 that enables image capture with respect to a lifting operation is placed.

Here, the object 7 reflects infrared rays, for example, an infrared reflector, to enable measurement of a relative distance or a relative position corresponding to an infrared transmission/reception time, and may be formed by coating or applying an infrared reflective material on an outer surface in a spherical shape.

The present embodiment having such a configuration, in which the lifting member 6 is lifted with respect to the sensing tube 5 so as to sense the movement pattern of the object 7 placed on the lifting member 6, apart from the movement change of the lung mimic 12 according to the change in the internal pressure of the lung mimic 12, may make it possible to expect the advantage of maximizing radiotherapy effects by sensing irregularities of breathing through vertical wave analysis over time according to the actual breathing pattern.

Figure 6:
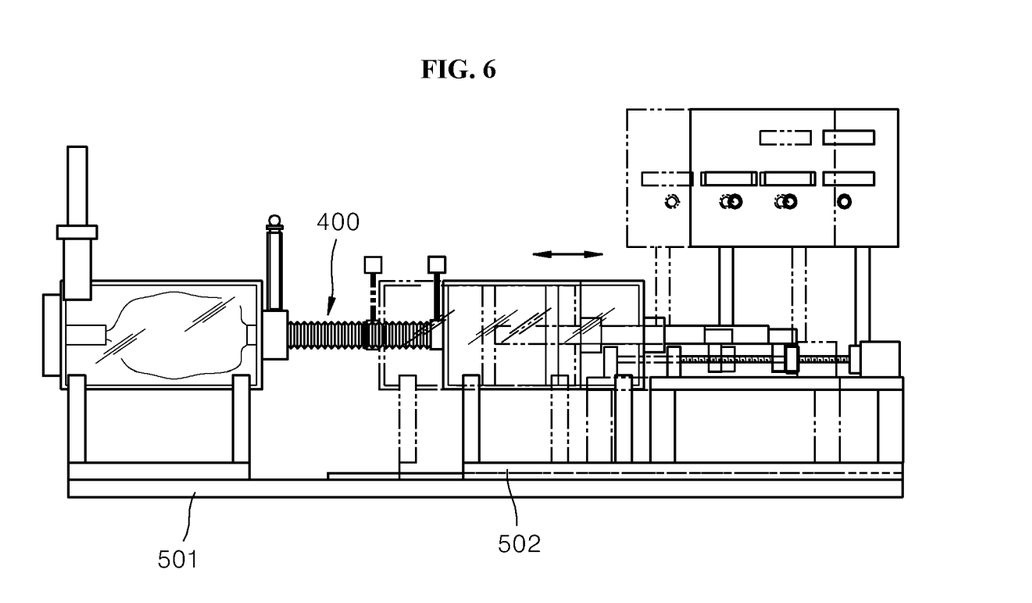
FIG. 6 is a view for explaining advantages of a lung phantom unit for radiotherapy according to another embodiment of the present invention.

Hereinafter, a lung phantom unit for radiotherapy according to another embodiment of the present invention will be described in detail with reference to FIG. 6.

The connection tube 400 employed in the present embodiment is in the form of a flexible corrugated tube so that length expansion and contraction is possible, unlike the embodiment described above.

The present embodiment including the connection tube 400 includes a first shelf 501 on which the lung simulation block is installed and a second shelf 502 on which the driving device is installed, wherein the first shelf 501 and the second shelf 502 are preferably installed to be movable relative to each other so as to enable length adjustment.

After all, the present embodiment, in which the relative distance between the lung simulation block and the driving device may be adjusted according to a site installation space or other installation environment, has the advantage of being utilized in various installation environments.

Figure 7:
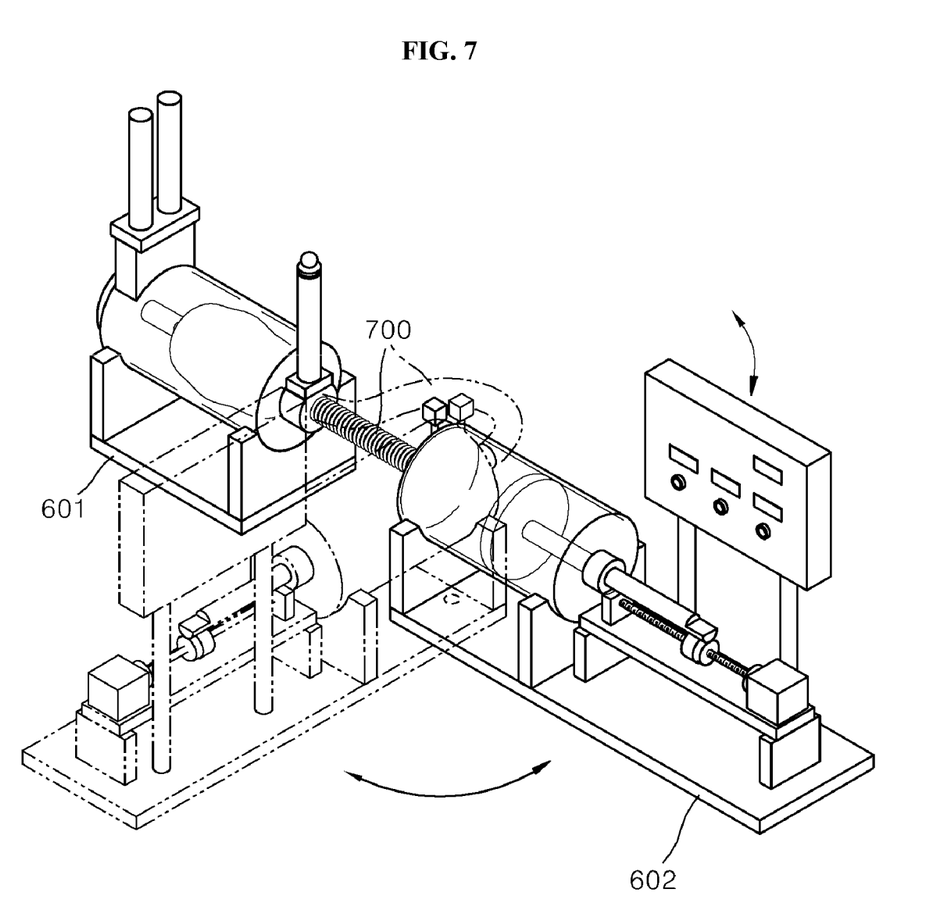
FIG. 7 is a view for explaining advantages of a lung phantom unit for radiotherapy according to another embodiment of the present invention.

FIG. 7 is a view for explaining advantages of a lung phantom unit for radiotherapy according to another embodiment of the present invention.

A connection tube 700 employed in the present embodiment is in the form of a flexible corrugated tube so that length expansion and contraction and bending are possible, similarly to the embodiment described with reference to FIG. 6.

The present embodiment includes a first shelf 601 on which a lung simulation block is installed and a second shelf 602 on which the driving device is installed, wherein the first shelf 601 and the second shelf 602 are installed to be rotatable relative to each other so as to enable angle adjustment.

The present embodiment having such a configuration has the advantage of enabling to install the lung simulation block and the driving device at positions spaced apart from each other even in a narrow installation space.

Although various embodiments of the present invention have been described above, the present embodiment and the drawings attached to the present specification only clearly show a part of the technical idea included in the present invention, and it will be apparent that all modifications and specific embodiments that may be easily inferred by those skilled in the art within the scope of the technical idea included in the specification and drawings of the present invention are included in the scope of the present invention.

What is claimed is:

1. A lung phantom unit for radiotherapy, comprising:
    a lung simulation block comprising a phantom human mimic filled with a liquid inside, a lung mimic accommodated in the phantom human mimic and contracted and expanded according to an inflow of external air, and a tumor mimic disposed inside the lung mimic;
    a phantom driving cylinder fluid-movably connected to the lung mimic at a position spaced apart from the lung simulation block;
    a driving device configured to compress and expand air accommodated in the phantom driving cylinder;
    a connection tube having one side communicatively connected to the phantom driving cylinder and the other side communicatively connected to the lung simulation block and formed to have a long length along a central axis direction of the phantom human mimic, so that an operation of the driving device is not affected by a magnetic field or an electric field formed by a capturing unit for securing an image of the lung simulation block;
    a sensing tube communicatively connected to the lung mimic and the phantom driving cylinder; and a lifting member comprising a rod portion installed on the sensing tube to be liftable and formed long along a lifting direction, and a mounting portion formed as a plate structure on an upper side of the rod portion and on which an object that enables image capture with respect to a lifting operation is placed.

2. The lung phantom unit for radiotherapy of claim 1, wherein the driving device comprises:
a motor;
a pressing disk movably installed in a chamber and moved by receiving power of the motor so as to compress and expand the air accommodated in the phantom driving cylinder; and
a pressing rod having one side connected to the motor and the other end connected to the pressing disk so as to be moved together with the pressing disk, to dynamically connect the motor and the pressing disk.

3. The lung phantom unit for radiotherapy of claim 2, wherein the driving device further comprises:
a nut member provided on the pressing rod; and a transfer screw formed long along an axis in one direction, connected to a drive shaft so as to be rotated together with the drive shaft of the motor, and screw-coupled with the nut member.

4. The lung phantom unit for radiotherapy of claim 1, wherein the lung simulation block is made of a non-metal material.

5. The lung phantom unit for radiotherapy of claim 1, wherein the connection tube is in the form of a flexible corrugated tube so that length expansion and contraction is possible.

6. The lung phantom unit for radiotherapy of claim 1, further comprising:
a first shelf on which the lung simulation block is installed and a second shelf on which the driving device is installed,
wherein the first shelf and the second shelf are installed to be movable relative to each other so as to enable length adjustment.

7. A lung phantom unit for radiotherapy, comprising:
a lung simulation block comprising a phantom human mimic filled with a liquid inside, a lung mimic accommodated in the phantom human mimic and contracted and expanded according to an inflow of external air, and a tumor mimic disposed inside the lung mimic;
a phantom driving cylinder fluid-movably connected to the lung mimic at a position spaced apart from the lung simulation block;
a driving device configured to compress and expand air accommodated in the phantom driving cylinder;
a connection tube having one side communicatively connected to the phantom driving cylinder and the other side communicatively connected to the lung simulation block and formed to have a long length along a central axis direction of the phantom human mimic, so that an operation of the driving device is not affected by a magnetic field or an electric field formed by a capturing unit for securing an image of the lung simulation block; and
a first shelf on which the lung simulation block is installed and a second shelf on which the driving device is installed,
wherein the first shelf and the second shelf are installed to be rotatable relative to each other so as to enable angle adjustment.

* * * * *